United States Patent [19]

Quadbeck-Seeger et al.

[11] 3,994,897
[45] Nov. 30, 1976

[54] PROCESS FOR THE MANUFACTURE OF CARBOXYLIC ACIDS FROM METHYL KETONES

[75] Inventors: Hans-Juergen Quadbeck-Seeger, Ludwigshafen; Werner Fliege, Otterstadt; Peter Tonne, Neustadt, all of Germany

[73] Assignee: BASF Aktiengesellschaft, Ludwigshafen (Rhine), Germany

[22] Filed: Mar. 6, 1975

[21] Appl. No.: 555,869

[30] Foreign Application Priority Data

Mar. 18, 1974 Germany............................ 2412855

[52] U.S. Cl............................ 260/268 SY; 260/249; 260/249.6; 260/260; 260/268 T; 260/293.51; 260/293.88; 260/295 R; 260/326.2; 260/347.3; 260/465.4; 260/515 R; 260/526 N; 260/540; 260/555 R

[51] Int. Cl.².................................... C07D 247/00

[58] Field of Search......... 260/347.3, 515 R, 526 N, 260/540, 295 R, 293.88, 326.2, 268 SY

[56] References Cited

UNITED STATES PATENTS 3,749,672    7/1973    Golton et al.......................... 252/95

Primary Examiner—Nicholas S. Rizzo
Assistant Examiner—Jose Tovar
Attorney, Agent, or Firm—Johnston, Keil, Thompson & Shurtleff

[57] ABSTRACT

Carboxylic acids are manufactured by reaction of methyl ketones with hypochlorites in the presence of bromine, iodine, haloamides, and/or polymerization inhibitors. The products are starting materials for the manufacture of dyes, plant protection agents, tanning agents, pickling agents, bates, vulcanizing agents and scents.

8 Claims, No Drawings

PROCESS FOR THE MANUFACTURE OF CARBOXYLIC ACIDS FROM METHYL KETONES

This application discloses and claims subject matter described in German Patent Application P 24 12 855.0, filed Mar. 18, 1974, which is incorporated herein by reference.

The invention relates to a process for the manufacture of carboxylic acids by reactions of methyl ketones with hypochlorites in the presence of bromine, iodine, haloamides and/or polymerization inhibitors.

It is known from Houben-Weyl, Methoden der organischen Chemie, volume 8, pages 415–416, that carboxylic acids can be manufactured by oxidation of methyl ketones with hypohalites in an aqueous medium. The publication recommends dispersing the ketone by means of oxidation-resistant emulsifiers or carrying out the reaction in the presence of dioxane; all the examples were carried out in this way. In most cases the reaction only takes place satisfactorily with hypobromite solutions, which are more expensive and less stable than hypochlorite solutions. For this reason alone, industrial utilization of the reaction is confined to special reactions with aromatic ketones.

It is an object of the present invention to provide a new process for the manufacture of carboxylic acids by a simpler and more economical method and in some cases in better yield and higher purity.

We have found that carboxylic acids are obtained advantageously from methyl ketones by reaction with hypochlorites in an aqueous medium if the keytone is reacted in the presence of bromine, iodine, haloamides of the formula

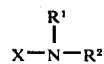
                I wherein $R^1$ is a sulfonic acid group, a sulfonate radical or a sulfonamide group, $R^2$ is hydrogen, an aliphatic radical, chlorine or bromine, X is chlorine, bromine or hydrogen and $R^1$ and $R^2$ can also, together with the adjoining nitrogen atom, be members of a heterocyclic radical which contains at least one sulfonyl group, adjacent to the nitrogen atom, or phosphonyl group, adjacent to the nitrogen atom, of the formula

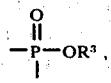

wherein $R^3$ is hydrogen or alkali metal, or $R^1$ and $R^2$ can together be the radical

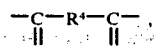

wherein $R^4$ is alkylene,

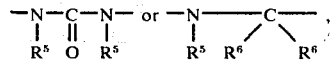

$R^5$ is hydrogen, chlorine or bromine and $R^6$ is an aliphatic radical, and/or in the presence of polymerization inhibitors.

Where pinacolone and sodium hypochlorite are used, the reaction can be represented by the following equation:

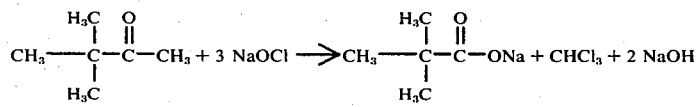

Compared to conventional processes, the process of the invention suprisingly gives carboxylic acids more simply and more economically and in some cases in better yield and better purity, and permits the manufacture, even on an industrial scale, of a large number of carboxylic acids by using a hypochlorite. Since the alkaline hypochlorite solution is more stable than the hypobromite solution and its strength barely decreases even after several days, the process of the invention is more reliable, more trouble-free and particularly suitable for industrial operation. Compared to conventional processes which use hypochlorite solutions, the process of the invention gives better overall results with regard to yield or purity of the end product, and a lower consumption of alkali metal hydroxide solution. The uneconomical addition of dioxane is no longer necessary, nor does the ketone have to be converted to a dispersion before preparing the starting mixture. The chloroform obtaind as a by-product is a valuable solvent and intermediate and can easily be isolated and used for other syntheses; this of particular value in industrial operation, in furthering the economy and simplicity of the process.

Preferred methyl ketones have the formula

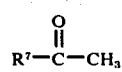
II and accordingly preferred carboxylic acids have the formula

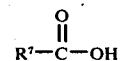
III wherein $R^7$ is an aliphatic radical, preferably alkyl of 1 to 12 carbon atoms or alkenyl of 3 to 12 carbon atoms and with, preferably, 1 or 2 double bonds, a cycloaliphatic radical, preferably cyclohexyl, an araliphatic radical, preferably aralkyl of 7 to 15 carbon atoms or aralkenyl of 8 to 15 carbon atoms, an aromatic radical, preferably phenyl or naphthyl, or a heterocyclic radical optionally linked to the keto group by alkylene of 1 to 4 carbon atoms or alkenylene of 2 to 4 carbon atoms, preferably a 5-membered or 6-membered heterocyclic ring, which may contain one or two nitrogen atoms or one oxygen atom, optionally linked to the keto group by alkylene of 1 to 4 carbon atoms or alkenylene of 2 to 4 carbon atoms. The above radicals and rings can also be substituted by groups and/or atoms which are inert under the reaction conditions, e.g. chlorine, bromine or alkyl of 1 to 4 carbon atoms; the sulfonic acid group or nitro may be present as substituents of a benzene nucleus.

The following methyl ketones are examples of suitable starting materials II: pinacolone, acetone, mesityl oxide, cinnamalacetone, 2-methylhept-4-en-6-one, 2-methylheptan-6-one, 2-methylhept-1-en-6-one, benzalacetone, furylideneacetone, dodecyl methyl ketone, cyclohexyl methyl ketone, benzyl methyl ketone, phenyl methyl ketone, β-naphthyl methyl ketone, 2-pyridyl methyl ketone, 2-piperidinyl methyl ketone, 2-piperazinyl methyl ketone and 2-pyrrolidinyl methyl ketone.

The other starting materials are aqueous hypochlorites, as a rule in the form of aqueous alkaline solutions. The methyl ketone is advantageously used in the form of aqueous suspensions of from 1 to 50% strength by weight. The aqueous hypochlorite solutions in general contain from 5 to 15, preferably from 12 to 14, % by weight of hypochlorite and may in addition contain from 0.2 to 2.5 moles, preferably from 1 to 2.1 moles, of alkali metal hydroxide per mole of hypochlorite. The initial mixture of the two starting materials in general contains a total of from 3 to 5, preferably from 3.1 to 4, moles of hypochlorite per mole of methyl ketone. Sodium hypochlorite and potassium hypochlorite are preferred.

The catalysts used are bromine, iodine, haloamides I and/or polymerization inhibitors, in general in amounts of from 0.0001 to 0.1, preferably from 0.001 to 0.05, mole of catalyst per mole of methyl ketone. Instead of the above catalysts, it is also possible to use compounds which form such catalysts under the reaction conditions, e.g. to use bromides and iodides in place of bromine or iodine. Water-soluble halides are preferred and are advantageously used in the form of their alkaline earth metal salts or, especially,, their alkali metal salts, e.g., calcium bromide, calcium iodide, magnesium bromide, magnesium iodide, lithium bromide, lithium iodide and especially sodium bromide or iodide or potassium bromide or iodide. Preferred haloamides I are those wherein $R^1$ is a sulfonic acid group, a sulfonate radical, preferably an alkali metal sulfonate radical such as a sodium sulfonate or potassium sulfonate radical, or a sulfonamide group, $R^2$ is chlorine, bromine, alkyl of 1 to 4 carbon atoms or, preferably, hydrogen, X is bromine, chlorine or preferably hydrogen, $R^1$ and $R^2$ can furthermore, together with the adjacent nitrogen atom, be members of a heterocyclic 5-membered or 6-membered ring which contains at least one sulfonyl group, adjacent to the nitrogen atom, or phosphonyl group, adjacent to the nitrogen atom, of the formula

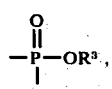

wherein $R^3$ is hydrogen or an alkali metal, especially sodium or potassium, or $R^1$ and $R^2$ together are the radical

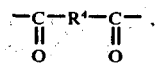

wherein $R^4$ is alkylene of 2 to 4 carbon atoms,

$R^5$ is hydrogen, chlorine or bromine and $R^6$ is alkyl of 1 to 4 carbon atoms, preferably methyl. A phenylene nucleus may be fused to the above heterocyclic ring. The heterocyclic ring advantageously contains two sulfonyl or phosphonoyl groups, adjacent to the nitrogen atom, or two or three sulfonamido or phosphonamido groups, and in particular these groups are present in one and the same ring where polynuclear heterocyclic radicals are concerned. The above preferred radicals may furthermore be substituted by groups or atoms which are inert under the reaction conditions, e.g. chlorine, bromine, alkyl of 1 to 4 carbon atoms or — as substituents of the phenyl nucleus — carboxyl or carboxylate groups.

Examples of catalysts which may be used are glutarimide, adipimide and succinimide; but preferably cyanuric acid, 5,5-dimethylhydantoin, trisulfamide, N-methyl-sulfamic acid, sodium triimidometaphosphate; appropriate mixtures of the above haloamides I. In particular, sulfamic acid and its salts, expediently its alkali metal salts such as the sodium salt or potassium salt, and sulfamide, optionally mixed with the above haloamides I, are preferred.

The polymerization inhibitors used are compounds which inhibit or greatly retard the polymerization of monomers and thus act as stabilizers for the monomers. These inhibitors may be gaseous, solid or liquid; preferred compounds are those which inhibit the polymerization of vinyl compounds and especially those which inhibit their free radical polymerization. Inhibitors which may be used with advantage are sodium nitrite or inorganic compounds or divalent sulfur, preferably hydrogen sulfide, alkali metal sulfides, e.g. sodium sulfide or potassium sulfide, alkali metal bisulfides, e.g. lithium bisulfide, sodium bisulfide and potassium bisulfide, ammonium sulfide and ammonium polysulfide. Compounds wherein only a part of the sulfur in the molecule is divalent, such as alkali metal thiosulfates, e.g. sodium thiosulfate, may also be used. Phenol and thiophenol are also suitable catalysts.

Amongst the polymerization inhibitors, particularly advantageous catalysts are nitrogen compounds of the formula

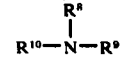      IV wherein $R^8$ is an aliphatic radical, preferably alkyl of 1 to 4 carbon atoms, a 6-membered heterocyclic radical which contains 3 nitrogen atoms, preferably triazinyl substituted by amino groups, the radical

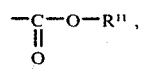

(wherein $R^{11}$ is an aliphatic radical, preferably alkyl of 1 to 4 carbon atoms), the radical

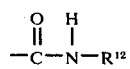

(wherein $R^{12}$ is hydrogen or cyano), cyano, the sulfonyl chloride or sulfonic acid group or the radical

(wherein $R^{13}$ is an aliphatic radical, preferably alkyl of 1 to 4 carbon atoms, an araliphatic radical, preferably aralkyl of 7 to 12 carbon atoms, amino or cycloalkylamino, preferably cyclohexylamino), or a sulfonate, preferably alkali metal sulfonate, group such as sodium sulfonate or potassium sulfonate, $R^9$ is an aliphatic radical, preferably alkyl of 1 to 4 carbon atoms, hydrogen, the radical

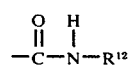

(wherein $R^{12}$ is hydrogen or cyano), phenyl or cyclohexyl, $R^{10}$ is an aliphatic radical, preferably alkyl of 1 to 4 carbon atoms, chlorine, bromine or preferably hydrogen, and furthermore $R^8$ and $R^9$ together with the adjacent nitrogen atom can be members of a 5-membered of 6-membered heterocyclic ring which may in addition contain an oxygen atom or an oxo group or contain the radical

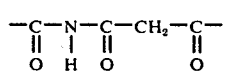

or the radical

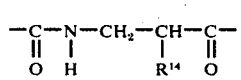

(wherein $R^{14}$ is alkyl of 1 to 4 carbon atoms), or $R^8$, $R^9$ and $R^{10}$ together with the adjacent nitrogen atom can be a bicyclic or tricyclic radical which in addition can contain from 1 to 3 nitrogen atoms, preferably a bicyclic or tricyclic radical of 2 to 4 nitrogen atoms and of 3 to 6 carbon atoms. The above preferred rings and radicals can also be substituted by groups which are inert under the reaction conditions, e.g. alkyl of 1 to 3 carbon atoms. The rings may contain double bonds. The nitrogen compounds can also be used in the form of their salts, e.g. p-toluenesulfamide can be used in the form of chloramine-T.

Preferred catalysts for the reaction are, in particular, di-aza-bicyclo [2,2,2] octane

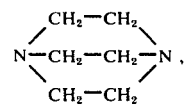

sodium thiosulfate, phenol, thiophenol, melamine

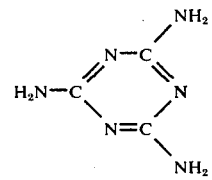

urea, cyanourea

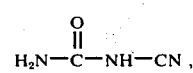

trimethylamine, N,N'-dicyclohexylsulfamide $C_6H_{11}$—NH-$SO_2$—NH—$C_6H_{11}$, sodium bisulfide, thymine

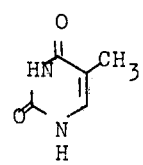

acetanilide, ethylurethane

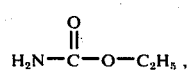

n-propylaminosulfochloride, biuret $NH_2$—CO—NH—CO—$NH_2$, isopropylaminosulfonic acid $(CH_3)_2CH$—NH—$SO_3H$, urotropin, cyanamide $H_2N$-C≡N, p-toluenesulfamide, pyrrolidone, barbituric acid

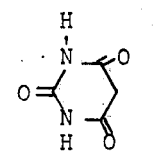

N-ethylacetamide, morpholine, piperidine, triethylamine, n-butylsulfamide, methanesulfonic acid amide, chloramine-T

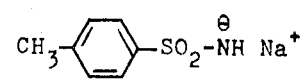

and sodium nitrite.

As a rule, the reaction is carried out at from −10° C to +62° C, preferably at from 10° to 50° C, under atmospheric or superatmospheric pressure, continuously or batchwise. The reaction may, e.g., be carried out as follows. The methyl ketone is introduced into a mixture of hypohalite, catalyst and water and the batch is kept at the reaction temperature for from 1 to 1,000 minutes. The end product is now isolated by conventional methods, e.g. by adding aqueous sodium bisulfite solution, acidifying the reaction mixture with a suitable acid such as sulfuric acid, separating off the organic phase formed and distilling the latter. It is also possible first to remove the chloroform layer which separates out, to acidify the aqueous phase, remove the organic phase which hereupon separates out and finally combine the organic phases.

The compounds which can be manufactured by the process of the invention are valuable starting materials for the manufacture of dyes, plant protection agents, tanning agents, pickling agents, bates, vulcanizing agents and scents. Their esters, especially with aliphatic alcohols, are scents, solvents, especially for ethereal oils and aromatic esters, and plasticizers.

With regard to the use of the compounds, reference may be made to Ullmanns Encyklopadie der technischen Chemie, volume 5, pages 108 to 120, volume 3, pages 310 and 465 et seq., and volume 19, pages 300 et seq.

The parts in the Examples which follow are by weight and bear the same relation to parts by volume as the kilogram to the liter.

EXAMPLE 1

50 parts of pinacolone are slowly added in portions in the course of 15 minutes to a mixture of 750 parts by volume of water, 660 parts by volume of sodium hypochlorite solution (containing 113 parts of sodium hypochlorite) and 0.5 part of amidosulfonic acid at 5° C. The mixture is cooled with ice water. The temperature rises to 23° C and the mixture turns cloudy; it is then stirred for a further 3 hours at room temperature. The chloroform formed is separated off, and the aqueous solution is acidified with 55 parts by volume of concentrated sulfuric acid (96% strength by weight) and steam-distilled. Pivalic acid (trimethylacetic acid) is separated off and the aqueous phase is extracted once with 40 parts by volume of ether. Yield: 42.8 parts of pivalic acid (83.8% of theory); melting at 33° C.

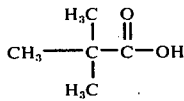

EXAMPLE 2

50 parts of mesityl oxide are added to a mixture of 900 parts by volume of sodium hypochlorite solution (containing 149 parts of sodium hypochlorite), 600 parts by volume of water and 0.5 part of sulfamide. The solution turns cloudy and the temperature rises to 60° C in the course of 10 minutes. The mixture is then stirred for a further 3 hours after which 20 parts by volume of concentrated sodium bisulfite solution (38% strength by weight) are added. The organic phase is separated off and the aqueous solution is acidified and then extracted once with 150 parts by volume of chloroform. The chloroform is distilled off the combined organic phases. 40 parts of β,β-dimethylacrylic acid (80% of theory) melting at from 60° to 63° C are obtained.

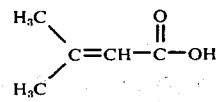

EXAMPLE 3

A solution of 86 parts of cinnamalacetone and 330 parts by volume of methanol is added in portions in the course of 3 hours to a mixture of 660 parts by volume of water, 900 parts by volume of sodium hypochlorite solution (containing 149 parts of sodium hypochlorite) and 0.8 part of thymine, sufficiently slowly to prevent the temperature rising above 60° C. After the temperature has fallen to 40° C, 8 parts of sodium bisulfite are added and the pH of the suspension is brought to 1–2 with concentrated hydrochloric acid. The mixture is cooled to 15° C and filtered, and the filter residue is rinsed with a little water and dried at 40° C. The yield of cinnamal acid (1-phenyl-4-carboxybutadiene) is 72 parts (82% of theory); the product melts at from 160° to 162° C.

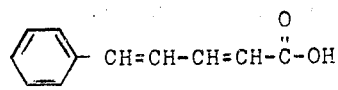

EXAMPLE 4

50 parts of 2-methylhept-4-en-6-one (95 per cent strength by weight) are added slowly and in portions, in the course of 20 minutes at from 31° to 36° C, to a mixture of 900 parts by volume of sodium hypochlorite solution (containing 149 parts of sodium hypochlorite. 600 parts by volume of water and 1 part of amidosulfonic acid. After a further reaction time of 1.5 hours at 40° C, 22 parts of an aqueous sodium bisulfite solution (38% by weight) are added. The organic phase which separates out is removed and combined with the organic layer obtained after acidifying the aqueous phase with concentrated sulfuric acid (96% strength by weight). The combined organic phases are freed from chloroform by distillation. 42 parts of 5-methyl-hex-2-en-1-oic acid (83% of theory) boiling at from 80° to 95° C at 0.05 mm Hg are obtained.

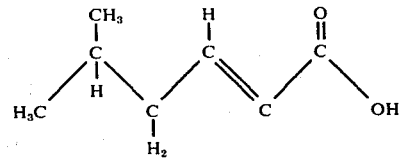

EXAMPLE 5

50 parts of 2-methylheptan-6-one are added slowly, in portions, to a mixture of 900 parts by volume of sodium hypochlorite solution (containing 149 parts of sodium hypochlorite), 200 parts by volume of water and 1.5 parts of diaza-bicyclo [2,2,2] octane at from 32° to 36° C. After a further reaction time of 1.5 hours at 40° C, 12 parts of sodium bisulfite are added, the organic phase is separated off, the aqueous phase is acidified and the organic phase which forms is again separated off. On distilling the combined organic phases, 22.1 parts of 5-methylhexanoic acid (43.6% of theory) are obtained at from 73° to 103° C at 0.05 mm Hg.

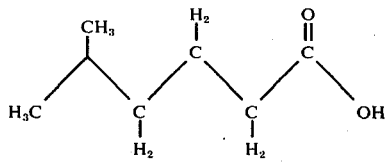

EXAMPLE 6

50 parts of 2-methyl-hept-1-en-6-one (90 per cent strength by weight) are reacted analogously to Example 4. The conversion is 95% and the yield is 19 parts of 5-methylhex-5-en-1-oic acid (41% of theory).

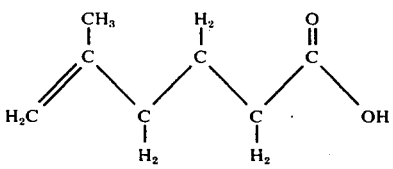

EXAMPLE 7

50 parts of benzalacetone are added slowly and in portions, in the course of 20 minutes at from 30° to 35° C, to a mixture of 900 parts by volume of sodium hypochlorite solution (containing 149 parts of sodium hypochlorite), 150 parts by volume of water and 1 part of potassium bromide. After a further reaction time of 1.5 hours at 40° C, the chloroform which has formed is separated off, the aqueous phase is acidified and the organic phase which forms is combined with the chloroform phase. The aqueous solution is extracted by shaking with a further 100 parts by volume of chloroform and the chloroform is distilled from the combined organic phases. 49.5 parts (98.5% of theory) of cinnamic acid melting at 122° C are obtained.

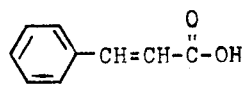

EXAMPLE 8

50 parts of furfurylideneacetone are added slowly and in portions, in the course of 20 minutes at from 30° to 35° C, to a mixture of 900 parts by volume of sodium hypochlorite solution (containing 149 parts of sodium hypochlorite), 660 parts by volume of water and 1.2 parts of melamine. After a further reaction time of 1.5 hours at 40° C, the mixture is worked up as in Example 7. 33 parts (65% of theory) of β-furyl-(2)-acrylic acid melting at from 130° to 135° C are obtained.

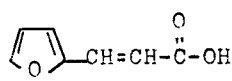

We claim:
1. A process for the manufacture of carboxylic acids from methyl ketones by reaction with hypochlorites in an aqueous medium, wherein the ketone is reacted in the presence of sulfamic acid, sulfamide, N-methyl sulfamic acid, alkali metal salts of sulfamic acid, N, N'-dicyclohexyl sulfamide, p-toluene sulfamide or its sodium salt, trisulfamide, n-butylsulfamide, methane sulfonic acid amide, isopropyl-amino sulfonic acid or n-propylaminosulfochloride.
2. A process as set forth in claim 1, wherein the reaction is carried out with from 3 to 5 moles of hypochlorite per mole of the methyl ketone starting material.
3. A process as set forth in claim 1, wherein the reaction is carried out with hypochlorite solutions containing from 5 to 15% by weight of hypochlorite.
4. A process as set forth in claim 1, wherein the reaction is carried out with from 0.0001 to 0.1 mole of catalyst per mole of methyl ketone starting material.
5. A process as set forth in claim 1, wherein the reaction is carried out with sodium nitrite, hydrogen sulfide, sodium sulfide, potassium sulfide, lithium bisulfide, sodium bisulfide, potassium bisulfide, ammonium sulfide, ammonium polysulfide, sodium thiosulfide, phenol or thiophenol.
6. A process as set forth in claim 1, wherein the reaction is carried out at from −10° C to +62° C.
7. A process as set forth in claim 1, wherein the reaction is carried out at from +10° C to +50° C.
8. A process as set forth in claim 1 wherein the amide is $H_2N-SO_2OH$.

* * * * *